US011304807B2

United States Patent
McNiven et al.

(10) Patent No.: US 11,304,807 B2
(45) Date of Patent: *Apr. 19, 2022

(54) INDEPENDENT SYSTEM FOR TRICUSPID VALVE REPAIR

(71) Applicant: Abbott Cardiovascular Systems Inc., Santa Clara, CA (US)

(72) Inventors: Sean A. McNiven, Menlo Park, CA (US); Laura M. Kalvass, Mountain View, CA (US); Benjamin L. Lee, Santa Clara, CA (US); Antonio N. Garcia, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 229 days.

This patent is subject to a terminal disclaimer.

(21) Appl. No.: 16/685,778

(22) Filed: Nov. 15, 2019

(65) Prior Publication Data

US 2020/0078173 A1 Mar. 12, 2020

Related U.S. Application Data

(63) Continuation of application No. 15/215,387, filed on Jul. 20, 2016, now Pat. No. 10,478,304.

(51) Int. Cl.
*A61F 2/24* (2006.01)

(52) U.S. Cl.
CPC .......... *A61F 2/2454* (2013.01); *A61F 2/246* (2013.01); *A61F 2/2436* (2013.01); *A61F 2/2466* (2013.01); *A61F 2220/0008* (2013.01)

(58) Field of Classification Search
CPC ...... A61F 2/2412; A61F 2/2427; A61F 2/243; A61F 2/2454; A61F 2/2439;
(Continued)

(56) References Cited

U.S. PATENT DOCUMENTS 6,165,183 A 12/2000 Kuehn et al.
7,563,267 B2 7/2009 Goldfarb et al.
(Continued)

FOREIGN PATENT DOCUMENTS

EP 3 017 792 A1 5/2016

OTHER PUBLICATIONS

Extended European Search Report dated Feb. 6, 2020 in Application No. EP 17831533.
(Continued)

*Primary Examiner* — Todd J Scherbel
*Assistant Examiner* — Mikail A Mannan
(74) *Attorney, Agent, or Firm* — Baker Botts L.L.P.

(57) ABSTRACT

A system for repairing a tricuspid valve and positioned at a distal end of a catheter having a proximal end and a distal end and a bore extending between the proximal end and the distal end. The system comprises an activation element extending along the bore, the activation element including a first push element and a first pull element; a second push element and a second pull element; a third push element and a third pull element; wherein the first push element, the second push element, and the third push element are independently slideable in relation to each other; a first lower jaw being pin connected to the first pull element; a second lower jaw being pin connected to the second pull element; a third lower jaw being pin connected to the third pull element.

19 Claims, 5 Drawing Sheets

(58) Field of Classification Search
CPC ...... A61F 2/2436; A61F 2/246; A61F 2/2466; A61F 2220/0008; A61F 2220/0091; A61B 2017/00243; A61B 2017/00783; A61B 17/28; A61B 17/2804; A61B 17/29; A61B 17/128; A61B 17/1285; A61B 17/22031; A61B 17/44; A61B 17/30; A61B 2017/2906; A61B 2017/3932; A61B 2017/2938; A61B 2017/2939; A61B 2017/301; A61B 2017/303; A61B 2017/1125

See application file for complete search history.

(56) References Cited

U.S. PATENT DOCUMENTS

| | | | |
|---|---|---|---|
| 2006/0229708 | A1 | 10/2006 | Powell et al. |
| 2009/0163934 | A1* | 6/2009 | Raschdorf, Jr. .. A61B 17/00234 606/139 |
| 2012/0179184 | A1 | 7/2012 | Orlov |
| 2013/0138121 | A1 | 5/2013 | Allen et al. |
| 2013/0338764 | A1 | 12/2013 | Thornton et al. |
| 2014/0039608 | A1 | 2/2014 | Eidenschink |
| 2015/0223793 | A1 | 8/2015 | Goldfarb et al. |
| 2015/0257877 | A1 | 9/2015 | Hernandez |
| 2015/0257883 | A1* | 9/2015 | Basude .............. A61B 17/0644 623/2.11 |
| 2016/0174979 | A1 | 6/2016 | Wei |

OTHER PUBLICATIONS

Vismara et al., "Transcatheter Edge-to-Edge Treatment of Functional Tricuspid Regurgitation in an Ex Vivo Pulsatile Heart Model," JACC 68(10):1024-1033 (2016).

U.S. Appl. No. 15/215,387 (U.S. Pat. No. 10,478,304), Jul. 20, 2016 (Nov. 19, 2019).
U.S. Appl. No. 15/215,387, Oct. 17, 2019 Issue Fee Payment.
U.S. Appl. No. 15/215,387, Jul. 17, 2019 Notice of Allowance.
U.S. Appl. No. 15/215,387, Apr. 8, 2019 Response to Non-Final Office Action.
U.S. Appl. No. 15/215,387, Jan. 10, 2019 Non-Final Office Action.
U.S. Appl. No. 15/215,387, Oct. 30, 2018 Response to Restriction Requirement.
U.S. Appl. No. 15/215,387, Aug. 3, 2018 Restriction Requirement.

* cited by examiner

INDEPENDENT SYSTEM FOR TRICUSPID VALVE REPAIR

REFERENCE TO RELATED APPLICATIONS

This application is a continuation of U.S. patent application Ser. No. 15/215,387, filed Jul. 20, 2016, now allowed, the contents of which is hereby incorporated by reference in its entirety.

BACKGROUND

This invention relates to the repair of a tricuspid valve exhibiting valve regurgitation. More particularly, the invention relates to apparatus and methods suitable for a less invasive repair of a tricuspid heart valve.

FIG. 1 is a cross-sectional view of the left and right ventricles of a human heart 14 in diastole. The figure shows how the tricuspid valve 21 connects together the chambers of the right atrium and the right ventricle, and controls the flow of blood between these two chambers.

FIG. 2 is a schematic view from above of a tricuspid valve of a human heart, showing the three leaflets of the valve namely the anterior leaflet 52, posterior leaflet 56, and the septal leaflet 54, which all converge on a common point of meeting at the center of the valve.

As used herein, the term "endovascular," refers to procedure(s) of the present invention that are performed with interventional tools and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach heart 14. As such, the methods and apparatus described herein generally do not require penetrations made directly through an exterior heart muscle, i.e., myocardium, although there may be some instances where penetrations will be made interior to the heart, e.g., through the interatrial septum to provide for a desired access route.

The atrioventricular valves are each located at a junction of the atria and their respective ventricles. The atrioventricular valve extending between the right atrium 30 and the right ventricle 12 has three valve leaflets (cusps) and is referred to as the tricuspid or right atrioventricular valve 21. The atrioventricular valve between the left atrium 32 and the left ventricle 10 is a bicuspid valve having only two leaflets or cusps 34 and is generally referred to as the mitral valve 20.

During operation of the heart 14, the valve leaflets open during diastole when the heart atria fill with blood, allowing the blood to pass into the ventricle. During systole, however, the valve leaflets are pushed together such that the free edges of the leaflets are closed against each other along a line of coaptation to prevent the back-flow of blood into the atria. Back flow of blood or "regurgitation" through the mitral valve 20 is facilitated to be prevented when the leaflets 34 are closed, such that the mitral valve 20 functions as a "check valve" which prevents back-flow when pressure in the left ventricle 10 is higher than that in the left atrium 32.

The mitral valve leaflets 34 are attached to the surrounding heart structure along an annular region referred to as the valve annulus 40. The free edges 36 of the leaflets 34 are secured to the lower portions of the left ventricle 10 through tendon-like tissue structures, known as chordae tendineae or chordae 42. The chordae 42 are attached to the papillary muscles which extend upwardly from the lower portions of the left ventricle and interventricular septum 46.

The tricuspid valve is similar to the mitral valve, but it is more complex in that it has three leaflets, as described above.

Tricuspid regurgitation, i.e., backward leakage of blood at the tricuspid heart valve, is typically caused by defective coaptation of the three leaflets against each other, and results in reduced pumping efficiency. Diagnosis of tricuspid regurgitation can be performed using visualization with transesophageal echocardiography or by echocardiography. In particular, defective leaflet coaptation and the site and direction of the regurgitant flow can be examined to evaluate likely modes of failure.

Tricuspid valve prolapse, i.e. degeneration of tricuspid valve leaflets, is the most common cause of tricuspid regurgitation in North America. Many cases of regurgitation can be repaired by modifications of the original valve in a procedure generally referred to as valvuloplasty. Valves that are heavily calcified or significantly compromised by disease may need to be replaced.

Successful methods have been developed for performing less invasive repairs to the mitral valve. In particular, such repairs can be performed on a beating heart such that the patient does not have to be placed on cardiopulmonary bypass.

One approach suitable for mitral valve repair is to introduce instruments via a transcatheter procedure into the heart by direct introduction through a passageway through the wall of the heart. Suitable gripping and fastening instruments have appropriate dimensions to fit through the cardiac catheter into the heart. The methods typically include gripping the edges of the two leaflets of the mitral valve, and securing them together using clasping, stitching, or suturing techniques. By connecting the leaves of the mitral valve together over a short length, the loss of tension in the leaves is reduced, and the remaining portions of the leaves have better coaptation and better perform the function of a one way valve by not permitting blood to flow in the wrong direction by regurgitation. The same approach as taken in repairing the mitral valve has been tried for repairing the tricuspid valve using clasps such as the clasp of the Mitra-Clip®.

However, methods for repairing the mitral valve do not apply conveniently to a method for repairing the tricuspid valve. One major difference is that while the mitral valve has only two leaflets extending parallel with each other and which are relatively easy to grasp simultaneously, the tricuspid valve has three leaflets 52, 54, 56 that come to a common point of meeting, as seen in FIG. 2. The mechanical problems involved in grasping all three leaflets simultaneously at a single point are far more complex than with the mitral valve, because the operator is not presented with two elongated edges to grasp, but with three triangulated points that must be grasped simultaneously. By doing this, the tension in the leaflets is increased, and coaptation is improved.

Accordingly, there is a need in the art for a novel and advantageous method to grasp and connect the three leaves of the tricuspid valve at the common point of their meeting. The present invention addresses these, and other needs.

SUMMARY OF THE INVENTION

In some embodiments, the invention is a system for repairing a tricuspid valve in a patient's heart, the system being positioned at a distal end of a catheter having a proximal end and a distal end and a bore extending between the proximal end and the distal end. The system comprises an activation element, extending along the bore. The activation element comprises a first push element and a first pull element slideable in relation to the first push element; a second push element and a second pull element slideable in relation to the second push element; and a third push element and a third pull element slideable in relation to the third push element. Under this configuration, the first push element, the second push element, and the third push element are independently slideable in relation to each other. The system further comprises a first lower jaw being pin connected to the first pull element; a first strut being pin connected to the first push element and also being pin connected to the first jaw. It further comprises a second lower jaw being pin connected to the second pull element; and a second strut being pin connected to the second push element and also being pin connected to the second jaw. It further comprises a third lower jaw being pin connected to the third pull element; and a third strut being pin connected to the third push element and also being pin connected to the third jaw.

In some embodiments, the first push element and the first pull element define a ratcheting means for preventing distal movement of the push element in relation to the pull element. In other embodiments, the system further included an elastic annulus that surrounds the activation element and which is positioned to apply a radially inward force on the ratcheting means. In some embodiments, the first push element defines a discontinuity surface means shaped for permitting separation of adjacent portions of the first push element. In some embodiments, the first pull element defines a discontinuity surface means shaped for permitting separation of adjacent portions of the first pull element. In some embodiments, the system further includes a first upper jaw that is connected to the first pull element, and further, in some embodiments the upper jaw defines gripping elements. And further, in some embodiments, the first upper jaw is connected to the first pull element by two pins that are spaced from each other. In some embodiments, the first upper jaw is configured to assume a compressed radius condition during delivery, and an expanded radius condition during deployment.

In another embodiment, the invention is a method of repairing a tricuspid valve having a first leaflet, a second leaflet, and a third leaflet in a heart of a patient. The method comprises inserting into the heart via transcatheter delivery a first set of opposing jaws, a second set of opposing jaws, and a third set of opposing jaws. The first set of opposing jaws is operated, independently of the second set of opposing jaws and the third set of opposing jaws, to grasp the first leaflet. Then, the second set of opposing jaws is operated, independently of the first set of opposing jaws and the third set of opposing jaws, to grasp the second leaflet. Finally, the third set of opposing jaws is operated, independently of the first set of opposing jaws and the second set of opposing jaws, to grasp the third leaflet. In some embodiments, the first set of opposing jaws is locked in a fixed position. In some embodiments, locking the first set of jaws in a fixed position includes applying a tension force extending circumferentially around a catheter delivering the first set of opposing jaws, the second set of opposing jaws, and the third set of opposing jaws. In some embodiments, the first set of opposing jaws is disconnected from a distal end of a delivery catheter. Further, in some embodiments, disconnecting the first set of opposing jaws includes withdrawing proximally a sheath surrounding the delivery catheter. In some embodiments, operating the first set of jaws includes moving a lower jaw towards an upper jaw.

These and other advantages of the invention will be more clearly understood when read in conjunction with the drawings and the detailed description of some of the embodiments.

DETAILED DESCRIPTION OF THE PREFERRED EMBODIMENTS

In some embodiments, as more clearly understood with reference to the drawings, the invention is a system for repairing the tricuspid valve in the heart of a patient via a transcatheter procedure. An objective of the system is to provide a mechanism that securely grips the three common points of meeting all three of the leaflets of a tricuspid valve simultaneously, at a central point where all three leaflets meet at the center of the valve. As a consequence of this connection, the tricuspid valve is converted into a valve having three separate orifices instead of only one orifice. However after being connected, the three orifices are formed by leaflets that close more completely during the systole and therefore more effectively fulfill a function of a one way fluid valve which is to prevent regurgitation.

Figure 1:
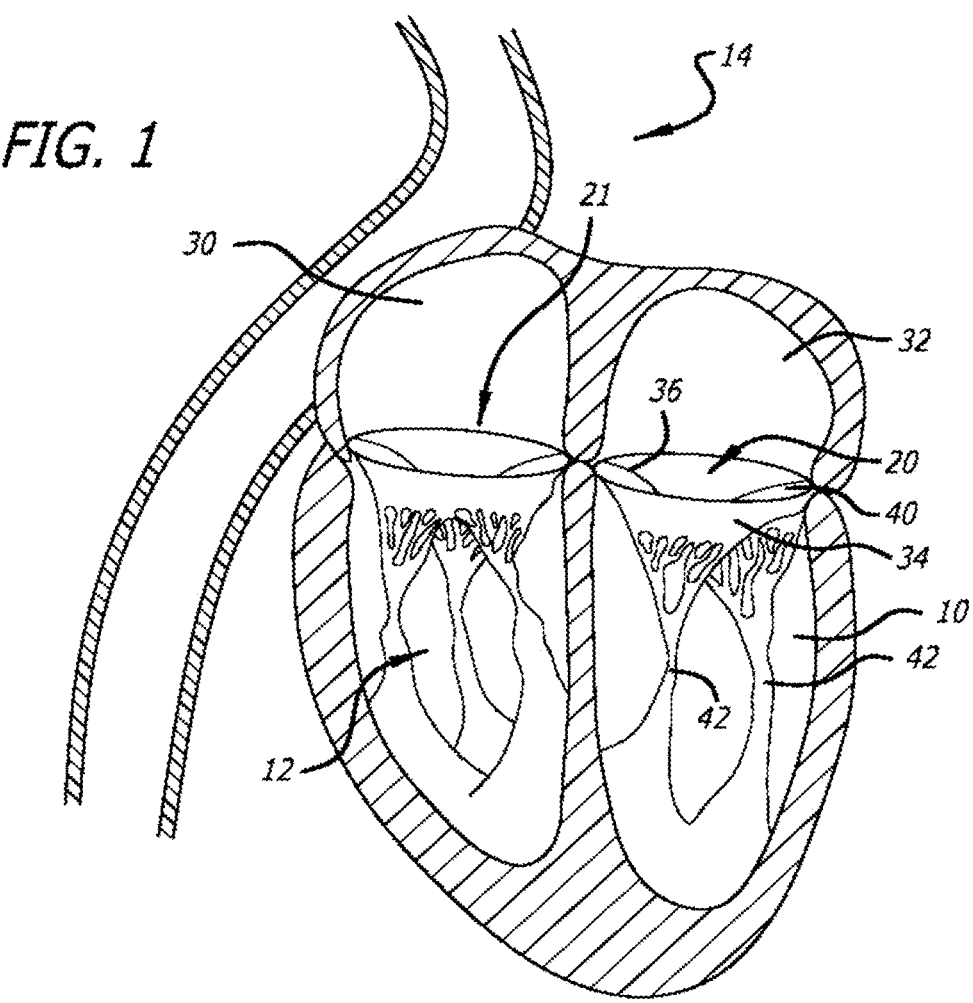
FIG. 1 is a cross-sectional view of the left and right ventricles of a human heart in diastole.
Figure 2:
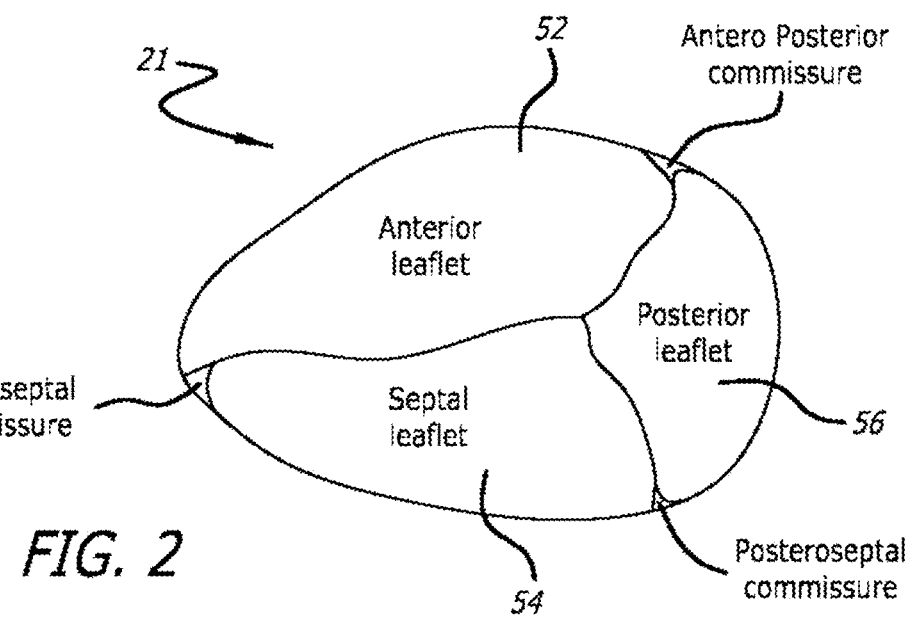
FIG. 2 is a schematic plan view of a tricuspid valve of a human heart, showing the three leaflets of the valve namely the anterior leaflet, posterior leaflet, and the septal leaflet, which all converge on a common point of meeting at the center of the valve.
Figure 3:
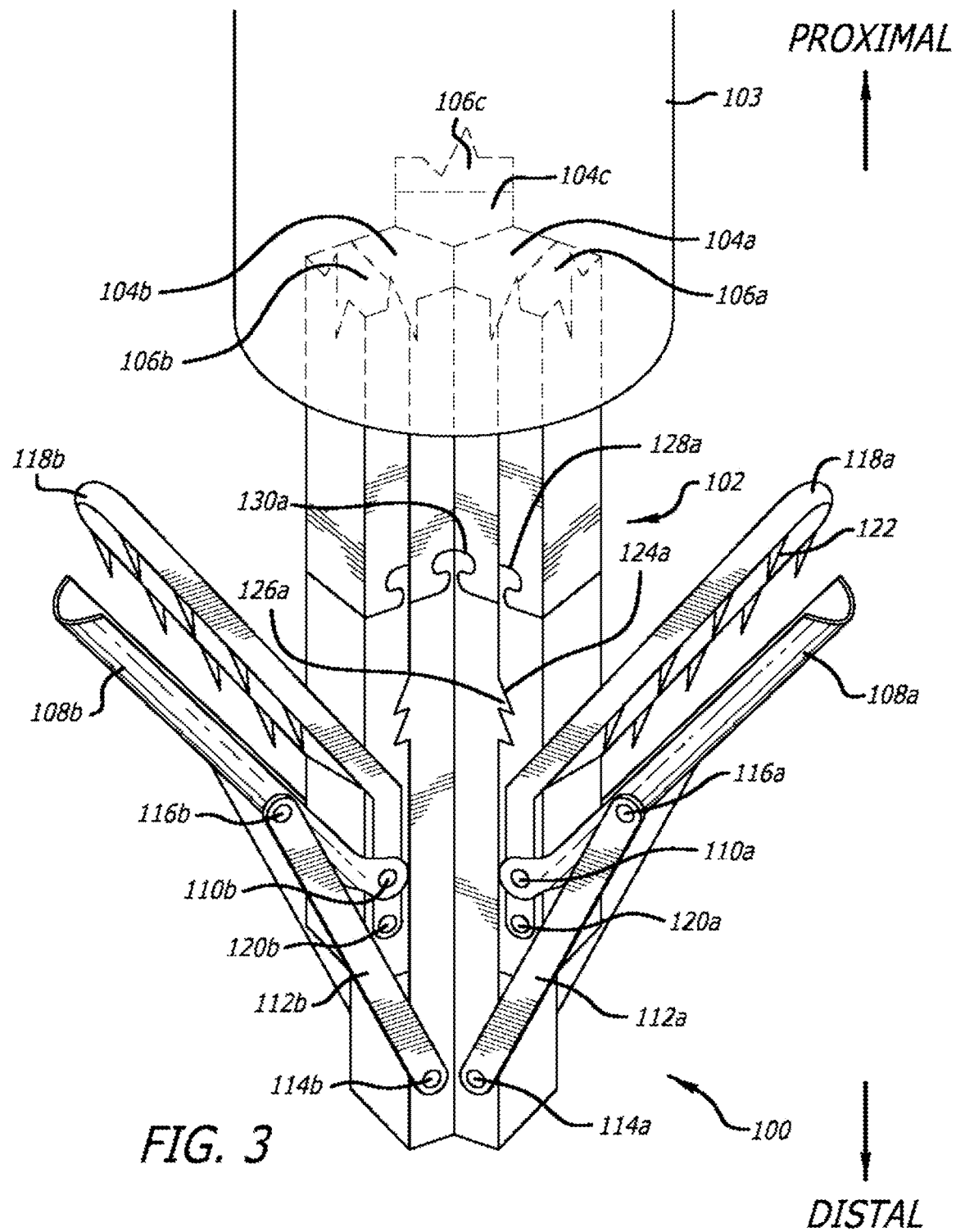
FIG. 3 is a perspective view of a system showing features of the invention, shown in an expanded condition in the heart of a patient. For clarity, element 130 is not included in this view.

FIG. 3 shows an exemplary system 100 which is positioned at the distal end of a delivery catheter. The system 100 extends along a central bore of the delivery catheter, and is configured to address problems found in the prior art. Extending between the proximal end of the catheter and the distal end, is an activation element 102. The activation element includes six sub-elements configured to be slidably movable independently of each other and in relation to each other. There are three push elements 104a, 104b and 104c; and there are three pull elements 106a, 106b, and 106c. As may be seen in FIGS. 3-5, the three push elements and the three pull elements are oriented to be rotationally offset from each other at an interval of 120 degrees about a central axis of the catheter. Further, each push element is associated with one pull element, thus forming three pairs of push and pull elements namely—104a and 106a; 104b and 106b; 104c and 106c. Within each pair of push and pull elements, the push and pull elements have the same orientation about the axis of the catheter. The names "push" and "pull" for these elements are used herein merely for identification and differentiation purposes, because each element may push and it may also pull, as described more fully below, depending on the needs of the operating physician.

As will be described in more detail below, each pair of push and pull elements is configured so that, upon deployment within the heart of a patient, the push element may be slidingly moved both proximally and distally in relation to the pull element. This relative movement permits an advantageous movement of further elements in the system 100 which are now described.

Attached to each pull element 106a, 106b, 106c is a lower jaw 108a, 108b, 108c respectively. The lower jaw is attached to each pull element by a first pin 110a, 110b, 110c to allow the lower jaw to rotate vertically about the first pin. (It will be appreciated that pin 110c is not shown in the figures, but that it is the equivalent of pins 110a and 110b. The same applies to all other elements numbered with a "c" suffix identified hereunder which are out of sight behind those equivalent elements having "a" and "b" suffixes and which are visible.)

Attached to each push element 104a, 104b, 104c is a strut 112a, 112b, 112c respectively. Each strut is attached at a first end to each push element by a second pin 114a, 114b, 114c respectively, and at a second end is attached to each lower jaw by a third pin 116a, 116b, 116c. It will be appreciated that when a pull element is pulled proximally in relation to a push element, the lower jaw will be forced by the strut to rotate upwards towards the central axis of the catheter.

Figure 4:
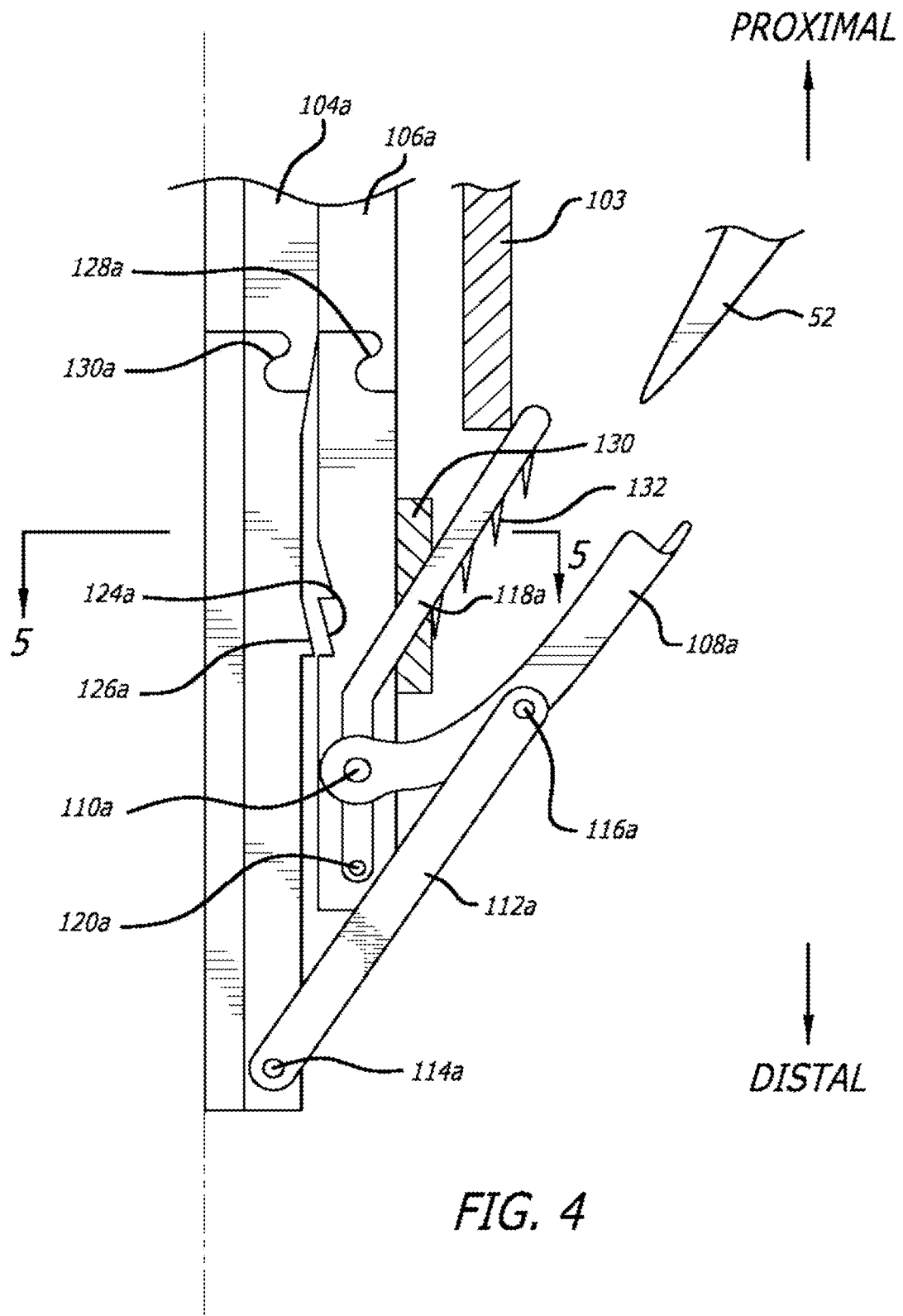
FIG. 4 is a partial sectional view of the system of FIG. 3, shown in vertical elevation. In this view, element 130 is shown in section.

Attached to each push element 106a, 106b, 106c is an upper jaw 118a. Each upper jaw is fixed in relation to the activation element by two pins, namely a fourth pin 120a, 120b, 120c and the first pin 110a, 110b, 110c. The upper jaw is shaped to be foldable in a delivery condition so that it extends parallel with the elongate axis of the activation element 102, where it may be contained inside a sliding outer sheath 103 (FIGS. 3-4), but to extend outwardly at an angle to the elongate axis in a deployed condition, as seen in FIGS. 3-4. The upper jaw may be supplied with gripping elements 122 configured to enhance the capture of one of the leaves of the tricuspid valve when the lower jaw is rotated upwards, as will be described below.

Further features of the system 100 include the following aspects: Between each push element and each pull element are mating surfaces shaped to act as ratchet and pawl. Specifically, the pull element 106a, 106b, 106c may include a ratchet 124, namely a concave shape; the push element 104a, 104b, 104c may include a pawl 126, namely a convex element. (It will be appreciated that the ratchet and pawl may be exchanged with each other to reach the same result.) The ratchet on the pull element may shaped with a sloping surface and a perpendicular surface, so that when the push element is slowly moved proximally in relation to the push element, the pawl falls into the ratchet and cannot slide back distally again, but it can advance further proximally. This "catch" feature has functional significance in that it allows an operator to collect a single leaf of the tricuspid valve between the lower jaw 108a, 108b, 108c and the upper jaw 118a, 118b, 118c, and to squeeze the leaf between the two jaws. The ratchet and pawl arrangement allows the leaf to be permanently captured without being released.

Another aspect of the system 100 is that each one of the push elements includes a discontinuity 128a, 128b, 128c and each one of the pull elements includes a discontinuity 130a, 130b, 130c. As may be understood with reference to FIGS. 3-4, these discontinuities are discontinuous surfaces shaped so that, so long as the push elements and pull elements remain in axial alignment, the discontinuity may transmit both a compression force and a tension force along their lengths. It will be appreciated that, so long as the push elements and the pull elements remain under and are contained by the sheath 103, they will maintain axial alignment. However, when axial alignment is lost, then the shape of the discontinuities allows a separation of adjacent portions of the elements at the location of the discontinuity to occur. This aspect has functional utility when the each of the three upper and lower jaws are successfully attached to the three leaves of the tricuspid valve. Once this objective has been achieved, the operator withdraws the sheath 103 from its position covering the discontinuities, to expose the discontinuities. The exposed push elements and pull elements can no longer maintain axial alignment due to the absence of a constraining force, and so the discontinuities permit adjacent portions of the push elements and pull elements to separate from each other, leaving the jaws and their related structure behind, and allowing the remainder of the catheter to be withdrawn from the site of the procedure in the patient's heart.

Figure 5:
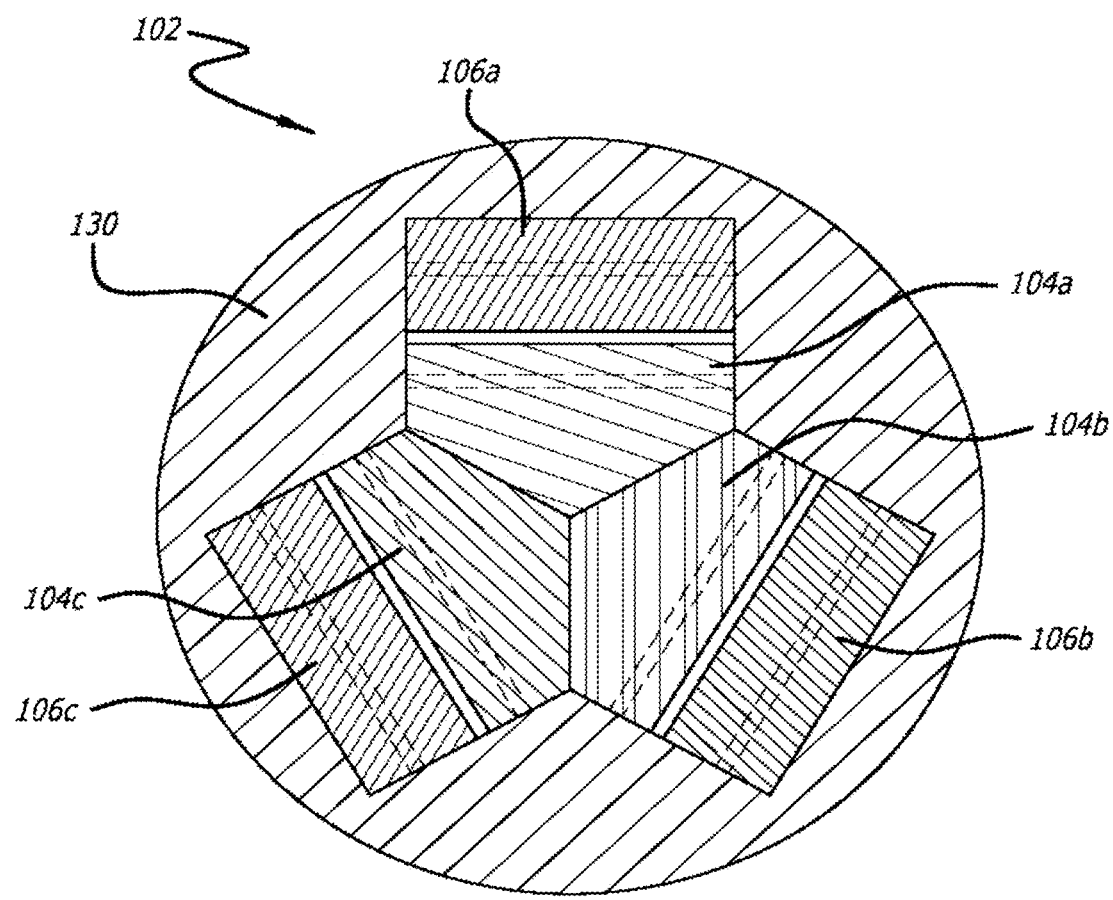
FIG. 5 is a sectional view of the system of FIG. 4, taken substantially along the line 5-5.

Yet another element of the system 100 is an elastic annulus 130 which is positioned to surround all of the push elements 104a, 104b, 104c and pull elements 106a, 106b, 106c together, as seen in FIG. 4-5. The elastic annulus 130 is positioned to surround these elements at the axial level of the ratchet and pawl, as seen in FIG. 4. The elastic annulus has the function of holding the push elements and pull elements together about the central axis of the activation element 102, yet at the same time allowing the ratchet system 100 to operate properly, by which the movement of the pawl in relation to the ratchet may force the push elements to part from the pull elements slightly, yet to snap back into contact with each other when the pawl is embedded within the ratchet. Even after the discontinuities 128a, 128b, 128c and 130a, 130b, 130c have been permitted to allow separation of adjacent portions of the push elements and pull elements, the elastic annulus 130 holds together the remaining structures supporting the upper jaws and lower jaws in their fixed positions, thus preventing these elements from simply falling apart.

Deployment of the system 100 may take the following steps. The catheter is threaded into the right atrium of the heart of the patient according to known methodology until the system 100 contained in the distal end of the catheter is positioned directly above the tricuspid valve. (See for example, U.S. Pat. No. 8,475,525 which is incorporated herein by reference.) The distal end is then advanced gently through the three leaflets of the tricuspid valve into the right ventricle. See FIG. 4, where one leaflet 52 is shown in relation to the system. At this point, the sheath 103 is withdrawn proximally by a short distance, sufficient to allow the upper jaw 118a to expand to its deployed configuration as seen in FIG. 4. Next, the push member 104a is moved distally to open the lower jaw 108a by an amount sufficient to receive one of the three leaflets 52 of the tricuspid valve as seen in FIG. 4. Then, the operator advances a first set of jaws towards the first leaflet 52. Such actions may be taken under visualization provided by a known system and method such as disclosed, for example, in U.S. Pat. No. 7,534,204, which is incorporated herein by reference. The first leaflet is captured between lower jaw 108a and upper jaw 118a. At this point, the corresponding push member 104a is moved proximally in relation to the pull member 106a, and this action will close the jaws. The push member 104a is moved further proximally by an amount sufficient to engage the pawl 126a with the ratchet 124a. This action locks the first set of jaws onto the leaflet 52, after which the jaws may be further tightened, but they may not be loosened due to the action of the ratchet means.

Once the first leaflet 52 is captured and locked according to this method, the operator moves his attention to the second leaflet 54, and when that is captured and locked, the operator moves to the third leaflet 56. It will be appreciated that the novel structure described permits the operator to approach each leaflet separately and independently for capture. The operator is not compelled to capture more than one leaf in a single action. Rather, individual attention may be brought to bear on each leaflet under visualization, thus permitting far greater focus and attention by the operator in overcoming problems in the prior art associated with capturing multiple leaves using one instrument in a single action.

Once all three leaflets are captured and the jaws locked, the operator withdraws the sheath 103 proximally to expose the discontinuities 128*a*, 128*b*, 128*c* and 130*a*, 130*b*, 130*c*. Adjacent portions of the push elements and pull elements proximal and distal of the discontinuities are thus allowed to separate from each other. The jaws are left behind in the heart, while the catheter and the balance of the system are withdrawn from the heart.

Figure 6:
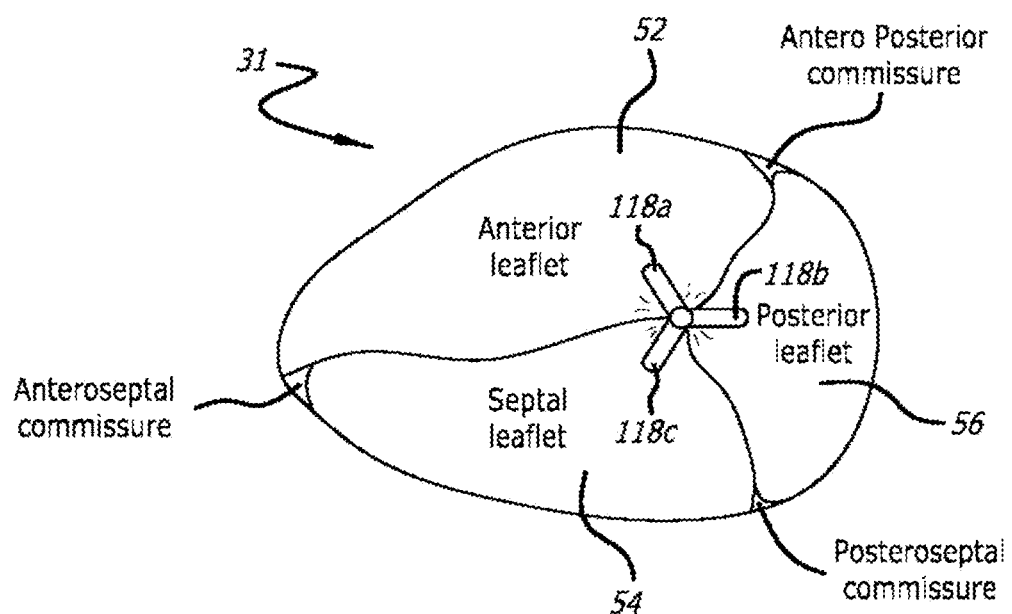
FIG. 6 is a view of the tricuspid valve as seen in FIG. 2, but having been joined at the center using aspects of the present invention.

The final result may be envisaged with reference to FIG. 6., which shows the three leaflets 52, 54, 56 captured at the point of their meeting in the center of the tricuspid valve 21. This action has the effect of tightening the leaflets along the lengths where they are contiguous with an adjacent leaf. The result is that the valve 21 now presents three separate bores for blood flow instead of only one. These three bores present a small cross sectional area for blood flow than a single bore. However, the improved coaptation of the leaflets is more efficient at preventing regurgitation, which is a highly desirable result.

Accordingly, there is described a novel system and method that addresses needs in the art for capturing and connecting the three contiguous points of a tricuspid heart valve. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A system for repairing a tricuspid valve in a patient's heart, the system comprising:
    a catheter having a proximal end and a distal end and a bore extending between the proximal end and the distal end;
    an activation element, extending through the bore, the activation element comprising a first push element and a first pull element slideable relative to the first push element, wherein the first push element and the first pull element are coupled by a ratchet to prevent distal movement of the first push element relative to the first pull element; and
    a first lower jaw being pivotally-connected to the first pull element.

2. The system of claim 1, wherein the first lower jaw is pivotally-connected to the first pull element by at least one pin.

3. The system of claim 1, further including a first strut extending between and pivotally-connected to the first push element and the first lower jaw, respectively.

4. The system of claim 3, wherein the first strut is pivotally-connected to each of the first push element and to the first lower jaw by at least one pin, respectively.

5. The system of claim 1, wherein the first push element defines a discontinuity shaped to permit separation of adjacent portions of the first push element.

6. The system of claim 1, wherein the first pull element defines a discontinuity shaped to permit separation of adjacent portions of the first pull element.

7. The system of claim 1, further including a first upper jaw pivotally-connected to the first pull element.

8. The system of claim 7, wherein the first upper jaw defines a gripping element to capture a leaflet between the first lower jaw and the first upper jaw.

9. The system of claim 7, wherein the first upper jaw is pivotally-connected to the first pull element by two pins spaced from each other.

10. The system of claim 7, wherein the first upper jaw has a compressed radius condition during delivery, and an expanded radius condition after deployment.

11. The system of claim 1, further including an elastic annulus surrounding the activation element and positioned to apply a radially inward force on the ratchet.

12. The system of claim 1, the activation element further including a second push element and a second pull element slideable in relation to the second push element.

13. The system of claim 12, the activation element further including a third push element and a third pull element slideable in relation to the third push element.

14. The system of claim 13, wherein the first push element, the second push element, and the third push element are independently slideable in relation to each other.

15. The system of claim 12, further including a second lower jaw being pivotally-connected to the second pull element by at least one pin.

16. The system of claim 15, further comprising a second strut being connected by one or more pins to the second push element and also being connected by one or more pins to the second lower jaw.

17. The system of claim 13, further comprising a third lower jaw being pivotally-connected to the third pull element by at least one pin.

18. The system of claim 17, further comprising a third strut being connected by one or more pins to the third push element and also being connected by one or more pins to the third lower jaw.

19. A method for repairing a tricuspid valve in a patient's heart, the method comprising:
    delivering an activation element using a catheter into the heart, the catheter having a proximal end and a distal end and a bore extending between the proximal end and the distal end, wherein the activation element extends through the bore and comprises a first push element and a first pull element;
    sliding the first push element relative to the first pull element, wherein the first push element and the first pull element are coupled by a ratchet to prevent distal movement of the first push element relative to the first pull element; and
    operating a first lower jaw, wherein the first lower jaw is pivotally-connected to the first pull element.

* * * * *